United States Patent [19]
Schwantes et al.

[11] Patent Number: 5,998,430
[45] Date of Patent: Dec. 7, 1999

[54] USE OF TROSPIUM CHLORIDE AND 2-COMPONENT SYSTEM FOR THE SAME

[75] Inventors: Ulrich Schwantes, Geisfeld; Albert Schaupp, Amlingstadt; Manfred Stöhrer, Murnau, all of Germany

[73] Assignee: Dr. R. Pfleger Chemische Fabrik GmbH, Bamberg, Germany

[21] Appl. No.: 08/971,423

[22] Filed: Nov. 17, 1997

[30] Foreign Application Priority Data

Nov. 27, 1996 [EP] European Pat. Off. .............. 96118939

[51] Int. Cl.⁶ ...................................................... A61K 31/44
[52] U.S. Cl. .............................................................. 514/299
[58] Field of Search ............................................. 514/299

[56] References Cited

FOREIGN PATENT DOCUMENTS

3546165A1  10/1987  Germany .

OTHER PUBLICATIONS

"Intravesikale Spasmolytika", Urologe (B) (1994)34:95, Springer Verlag, Jan. 1994.
Ultrasound Studies of the Effect of Trospium Chloride on Gall Bladder Kinetics, Drug Research, 42(II) Nr. 12 (1993).
Nonoperative Management of Urinary Incontinence, Current Opinion in Obstetrics and Gynecology, 1996 8:347–350.

*Primary Examiner*—Zohreh Fay
*Attorney, Agent, or Firm*—Roberts & Mercanti, L.L.P.

[57] ABSTRACT

Compositions of the anticholinergic agent trospium chloride suitable for localized administration are provided, in the form of an aqueous solution having a pH-value of ≧4.5, that is prepared prior to administration. Methods of using the provided compositions for treating dysfunctions of the bladder and the urinary system are also provided. The treatment methods are characterized by the intravesicular administration of the inventive composition into the bladder of a patient in need thereof

8 Claims, No Drawings

USE OF TROSPIUM CHLORIDE AND 2-COMPONENT SYSTEM FOR THE SAME

FIELD OF THE INVENTION

The present invention relates to sterile, 2-component medicinal formulations of trospium chloride that are useful for the localized treatment of urinary tract disorders, e.g., dysfunctional bladder, as well as to methods of making and using the same.

BACKGROUND OF THE INVENTION

Trospium chloride is an agent that has been known for several decades (cf. German patent 1 194 422) as an anticholinergic that is useful, for example, as a spasmolytic agent. This active agent has been available as an orally administrable, solid administration form (tablets and dragees), for intravenous or intramuscular injection as an injection solution and for rectal administration as suppositories and is mainly used for the treatment of bladder dysfunctions (urge incontinence, detrusorhyperreflexia). When these administration forms are used, losses of trospium chloride occur during the transport of the agent from the administration point to the action point. These losses are due to the excretion and metabolism processes occurring during systematic passage. In the case of the oral and rectal administration forms, losses are also due to poor absorption of trospium chloride, a quaternary ammonium compound, from the intestinal lumen into the system. In addition, with such active agent administration types, the typical side effects for anticholinergics, such as heart rate increases, dryness of the mouth, accommodation difficulties, etc. become disadvantageously noticeable.

Other anticholinergics, which as a result of their molecular structure constitute tertiary amines (e.g. oxybutynin), are absorbed to a greater extent following intravesicular instillation than following the administration of equivalent oral dosages (Massad C. A., Kogan B. A. & Trigo/Rocha F. E.: The Pharmacokinetics of intravesical and oral oxybutynin chloride. *J. Urol.* 148: 595/597, 1992). Thus, intravesical instillation of tertiary amine anticholinergics will not limit undesired anticholinergic side effects, because intravesicular absorption of tertiary amines will result in systemic effects at the target organ (e.g., heart, salivary gland, eye).

The problem to be solved by the present invention is consequently to prevent the disadvantages of the existing trospium administration forms, but still provide for administration by the patient, so that there is no need for clinical personnel or a doctor.

SUMMARY OF THE INVENTION

In order to solve these and other problems, the invention provides for the use of trospium chloride for the preparation of a medicinal formulation based on a sterile, aqueous solution, in the treatment of bladder dysfunctions and the urinary system. The use is characterized by the intravesical administration of trospium chloride by means of a catheter inserted directly into the bladder, the aqueous solution being prepared with a pH-value$\geq$4.5, prior to administration.

The invention also provides for the use of a medicinal formulation, characterized in that a 2-component system is used, which comprises the active agent trospium chloride in solid or dissolved form as the first component and an aqueous solvent for the same as a second component separate therefrom, in which the first component is dissolved or diluted in the use state.

The invention also provides a 2-component system, comprising the active agent trospium chloride in solid or dissolved form as the first component and a solvent for the same as a separate, second component, in which the first component can be dissolved or diluted in the use state and the resulting solution can be introduced at a pH-value$\geq$4.5 by means of a bladder catheter directly into the bladder for the treatment of bladder dysfunctions and the urinary system.

The invention further provides for the use of trospium chloride for the preparation of a medicinal formulation based on a sterile, aqueous solution, in the treatment of bladder dysfunctions and the urinary system, characterized by the intravesical administration by means of a bladder catheter directly into the bladder, based on a sterile, aqueous solution of pH-value$\geq$4.5, prepared prior to administration, from a first component of 5.0 to 35.0 mg of dissolved or solid trospium chloride and a second component of 20 to 40 ml of sodium chloride solution with 0.9% NaCl.

In addition, the invention provides for the use of trospium chloride for the preparation of a medicinal formulation based on a sterile, aqueous solution in the treatment of bladder dysfunctions and the urinary system, characterized by intravesical administration via a bladder catheter directly into the bladder and based on a sterile, aqueous solution with approximately 0.9% sodium chloride of pH-value$\geq$4.5 and, prior to administration, prepared from a first component consisting of 5 to 35 mg of lyophilized, solid or dissolved trospium chloride and a second component consisting of 20 to 40 ml of sodium chloride solution.

These features of the invention provide excellent results and obviate the disadvantages of the known administration forms.

DETAILED DISCLOSURE OF THE INVENTION

Accordingly, the invention provides for an aqueous trospium chloride solution prepared from two components, as described above. For the aqueous solution to remain stable for a long time during storage and transportation, the pH-value should be lower than 4.5. However, such a solution has never been considered suitable for administration to the bladder and is also unacceptable for physiological reasons. Therefore the invention assumes that the aqueous solution is prepared prior to administration with a pH-value equal to or greater than 4.5, in order to exclude from the outset ageing, storage and transportation problems.

It is particularly advantageous to prepare said aqueous solution with a pH-value$\geq$4.5 immediately prior to administration, in order to prevent any decomposition of the active agent trospium chloride. In particular, the pH-value of the inventive formulation is 5.0 to 7.5, so that it falls entirely within the pH-value range of the normal urine of healthy humans. In order to adequately contact all relevant areas of the bladder wall with the active substance, advantageously, liquid volumes of approximately 20 to 40 ml are necessary, because even in the case of a greatly reduced bladder capacity, the bladder still has volumes of approximately 150 to 300 ml and consequently a large, inner surface. While intravesical instillation provides adequate pharmacological action on the bladder muscle, the trospium chloride active agent, in contrast to the other anticholinergics discussed above, does not pass into the blood in significant quantities. This was confirmed by measuring plasma concentrations of trospium chloride after intravesicular instillation of 7.5 mg trospium chloride/20 ml for a period of 12 hours. At no time plasma concentrations were detected that were above the detection limit of the sensitive, validated measuring method.

In addition, a study performed on beagles concerning the local compatibility of trospium chloride following once daily intravesical instillation over a period of 4 weeks, revealed that the selected formulation did not lead to local adverse effects to the bladder tissue.

The advantage of the selected composition ranges for pH and osmolality of the trospium chloride solution of the invention is also made clear by an additional study carried out with a trospium chloride preparation of a different composition and by reports concerning the effects of oxybutynin in rabbits. Inflammatory processes were detected in the region of the bladder tissue after histological evaluation. The latter study described the intravesical instillation of crushed tablets in rabbits (Landau E. H., Fung L. C. T., Thorner P. S., Mittelman M. W., Jayanthi V. R., Churchill B. M., McLorie G. A., Steckler R. E. & Khoury A. E.: Histologic studies of intravesical oxybutynin in the rabbit, *J. Urol*, 153; 2022/2024, 1995).

It is also conceivable for the individual components of the 2-component solution to have different pH-values but which, immediately following mixing/dissolving, provide pH-values ranging from 4.5 to 7.5. Thus, the trospium chloride can e.g., have an acid pH-value of approximately 2.0, which is then raised into the range according to the invention of 4.5 to 7.5 by the addition to the aqueous solvent of a corresponding quantity of caustic soda solution.

Great significance is also attached to the sterility of the solution introduced into the bladder, as occurs in the invention, in conjunction with the avoidance of urinary tract infections.

It will be appreciated that the active agent trospium chloride acts as an anticholinergic, i.e. it occupies receptors of the parasympathetic nervous system, without causing the effects induced by the natural neurotransmitter acetyl choline (neurotropic action). The anticholinergic power of trospium chloride in vitro is 20 times greater than that of oxybutynin (Eckert R. E., Wilhelm A., Schwantes U., Utz J. Alloussi S., Trautwein W. & Ziegler M., Modulation of the cytoplasmic $Ca^{2+}$ concentration of isolated myocytes of the detrusor vesicae by anticholinergics, Akt. Urol. 26, 46, 1995). Moreover, internal investigations revealed that trospium chloride acts also directly on the smooth muscle cells of the detrusor (musculotropic action) through an inhibition of the basal $Ca^{2+}$ flow. These musculotropic characteristics are particularly important in the case of direct administration to the bladder.

What is claimed is:

1. A method of using trospium chloride for the preparation of a medicinal formulation based on a sterile, aqueous solution, in the treatment of bladder dysfunctions and the urinary system, characterized by the intravesical administration by means of a bladder catheter directly into the bladder, the aqueous solution being prepared with a pH-value≧4.5 prior to administration.

2. The method according to claim 1, characterized in that a 2-component system is used, which comprises the active agent trospium chloride in solid or dissolved form as the first component and an aqueous solvent for the same as a second component separate therefrom, in which the first component is dissolved or diluted in the use state.

3. A method of using trospium chloride for the preparation of a medicinal formulation based on a sterile, aqueous solution, in the treatment of bladder dysfunctions and the urinary system, characterized by the intravesical administration by means of a bladder catheter directly into the bladder, based on a sterile, aqueous solution of pH-value≧4.5 prepared prior to, administration from a first component of 5.0 to 35.0 mg of dissolved or solid trospium chloride and a second component of 20 to 40 ml of sodium chloride solution with 0.9% NaCl.

4. The method according to claim 3 characterized by intravesical administration via a bladder catheter directly into the bladder and based on a sterile, aqueous solution with approximately 0.9% sodium chloride of pH-value≧4.5 and, prior to administration, prepared from a first component consisting of 5 to 35 mg of lyophilized, solid or dissolved trospium chloride and a second component consisting of 20 to 40 ml of sodium chloride solution.

5. A method of treating a patient having bladder or urinary system dysfunction, comprising administering a sterile, aqueous solution of trospium chloride through a catheter directly into the bladder of the patient, said aqueous solution having a pH of about 4.5 or greater.

6. The method of claim 5 further comprising preparing said sterile, aqueous solution of trospium chloride from a first and second component, wherein said first component is trospium chloride in solid or dissolved form, said second component is an aqueous solvent and the method comprises mixing said first and second components.

7. A method of treating a patient having bladder or urinary system dysfunction, comprising catheterizing the bladder of said patient, and administering an effective amount of a sterile, aqueous solution of trospium chloride through said catheter directly into said bladder, said aqueous solution having a pH of about 4.5 or greater, said aqueous solution being prepared, prior to administration, from a first component of from 5.0 to 35.0 mg of lyophilized trospium chloride and a second component of from 20 to 40 ml of 0.9% sodium chloride solution.

8. The method of claim 7 wherein said urinary system dysfunction is detrusorhyperreflexia.

* * * * *